(12) United States Patent
Ovsyanko et al.

(10) Patent No.: US 9,157,891 B2
(45) Date of Patent: Oct. 13, 2015

(54) BIOSENSOR WITH QUADRUPOLE MAGNETIC ACTUATION SYSTEM

(75) Inventors: Mikhail Mikhaylovich Ovsyanko, Eindhoven (NL); Xander Jozef Antoine Janssen, Se Bavel (NL); Ben De Clercq, Alken (BE)

(73) Assignee: Koninklijke Philips N.V., Eindhoven (NL)

( * ) Notice: Subject to any disclaimer, the term of this patent is extended or adjusted under 35 U.S.C. 154(b) by 943 days.

(21) Appl. No.: 13/124,333

(22) PCT Filed: Oct. 6, 2009

(86) PCT No.: PCT/IB2009/054373
§ 371 (c)(1),
(2), (4) Date: Apr. 14, 2011

(87) PCT Pub. No.: WO2010/044006
PCT Pub. Date: Apr. 22, 2010

(65) Prior Publication Data
US 2011/0199080 A1   Aug. 18, 2011

(30) Foreign Application Priority Data

Oct. 16, 2008 (EP) .................................. 08166797

(51) Int. Cl.
G01R 33/04 (2006.01)
G01N 27/74 (2006.01)
G01R 33/12 (2006.01)
G01N 35/00 (2006.01)

(52) U.S. Cl.
CPC .......... G01N 27/745 (2013.01); G01R 33/1269 (2013.01); G01N 35/0098 (2013.01)

(58) Field of Classification Search
CPC ............ G01N 27/745; G01N 35/0098; G01R 33/1269
USPC ................. 73/54.18, 514.39, 519.01, 520.01; 435/173.1–173.9; 436/149–151, 806; 422/186, 186.1–186.2; 700/266; 702/19, 22

See application file for complete search history.

(56) References Cited

U.S. PATENT DOCUMENTS 5,466,574 A   11/1995   Liberti
5,968,820 A   10/1999   Zborowski
(Continued)

FOREIGN PATENT DOCUMENTS

CN   101111769 A   1/2008
JP   2002531811 A   9/2002
(Continued)

OTHER PUBLICATIONS

Yellen, Benjamin B. et al "Traveling Wave Magnetophoresis for High Resolution Chip Based Separations" Lab on a Chip, 2007, vol. 7, pp. 1681-1688.
(Continued)

Primary Examiner — Shogo Sasaki

(57) ABSTRACT

The present invention provides a biosensor comprising means (5) for accommodating a fluid sample having a sensor surface at its bottom and means for detecting particles accumulated at and/or proximate the sensor surface. The biosensor further comprises a quadrupole magnetic unit (1, 2, 3, 4) adapted to provide a magnetic field gradient at the sensor surface, wherein the unit is arranged below the sensor surface.

17 Claims, 7 Drawing Sheets

(56) References Cited

U.S. PATENT DOCUMENTS 6,361,749 B1 3/2002 Terstappen
2006/0194327 A1 8/2006 Kahlan

FOREIGN PATENT DOCUMENTS

| | | |
|---|---|---|
| JP | 2008528998 A | 7/2008 |
| WO | 2005111614 A1 | 11/2005 |
| WO | 2007085980 A1 | 8/2007 |
| WO | 2007129275 A2 | 11/2007 |
| WO | 2008107827 A1 | 9/2008 |

OTHER PUBLICATIONS

Ahn, Chong H. et al "A Fully Integrated Micromachines Magnetic Particle Separator" Journal of Microelectromechanical Systems, vol. 5, No. 3, Sep. 1996, pp. 151-158.

Top view setup

Cross section

Straight field

Field under 45°

BIOSENSOR WITH QUADRUPOLE MAGNETIC ACTUATION SYSTEM

FIELD OF THE INVENTION

The present invention relates to a magnetic-label biosensor with a quadrupole magnetic actuation system.

BACKGROUND OF THE INVENTION

The demand for biosensors is increasingly growing these days. Usually, biosensors allow for the detection of a given specific molecule within an analyte, wherein the amount of said molecule is typically small. For example, one may measure the amount of drugs or cardiac markers within saliva or blood. Therefore, target particles, for example super-paramagnetic label beads, are used which bind to a specific binding site or spot only, if the molecule to be detected is present within the analyte. One known technique to detect these label particles bound to the binding spot is frustrated total internal reflection (FTIR). Therein, light is coupled into the sample at an angle of total internal reflection. If no particles are present close to the sample surface, the light is completely reflected. If, however, label particles are bound to said surface, the condition of total internal reflection is violated, a portion of the light is scattered into the sample and thus the amount of light reflected by the surface is decreased. By measuring the intensity of the reflected light with an optical detector, it is possible to estimate the amount of particles bound to the surface. This allows for an estimate of the amount of the specific molecules of interest present within the analyte or sample.

This technique as well as other magnetic-label sensors, in particular biosensors, critically depend on the magnetic attraction of the beads or magnetic labels, also referred to as actuation. Magnetic actuation is in particular essential in order to increase the performance (speed) of the biosensor for point-of-care applications. The direction of the magnetic actuation can be either towards the surface or sensor area where the actual measurement is carried out or away from this sensor surface. In the first case, magnetic actuation allows for the enhancement of concentration of magnetic particles near the sensor surface, thus speeding up the binding process of the magnetic particles to the sensor area. In the second case, particles are removed from the surface which is called magnetic washing. Magnetic washing can replace the traditional wet washing step. It is more accurate and reduces the number of operating steps.

In more complex applications, several binding spots may be provided on a tiny surface. It may then be necessary to first accumulate the particles or labels at a first binding site and after a washing step to drive the magnetic labels towards another binding site. Such applications afford a large amount of control of the magnetic field generated in order to provide precise and predetermined forces onto the magnetic label particles.

SUMMARY OF THE INVENTION

It is therefore an object of the present invention to provide an improved magnetic-label biosensor, which allows for an enhanced amount of control of the forces onto the magnetic label particles. It is another object of the present invention to provide an improved biosensor which is more flexible and can be used for different kinds of applications.

These objects are achieved by the features of the claims.

The present invention provides a biosensor comprising means for accommodating a fluid sample having a sensor surface at its bottom and means for detecting particles accumulated at and/or proximate the sensor surface. The biosensor further comprises a quadrupole magnetic unit adapted to provide a magnetic field gradient at the sensor surface, wherein the unit is arranged below the sensor surface.

An example for the means for accommodating a fluid sample is a sample cell such as a cartridge or sample chamber, which is adapted to receive and contain a fluid sample. The sample cell may, e.g., be a cartridge or cuvette with a sensor surface at its bottom, which is in fluid contact with the sample volume of the cartridge.

Any detector suitable for detecting magnetic particles may be used as means for detecting particles accumulated at and/or proximate the sensor surface. Preferably, an optical detector is used. A particularly preferred embodiment of the biosensor utilizes an optical detector based on FTIR (frustrated total internal detection).

In a particularly preferred embodiment of the present invention, the quadrupole magnetic unit comprises four magnetic subunits which are independently controllable. The quadrupole magnetic unit may comprise, e.g., four electromagnetic coils, which are independently controllable by providing an electric current to said coils separately. This allows for the generation of specific patterns of the magnetic field and/or the magnetic field gradient at the sensor surface. For example, only two or three of the magnetic subunits may be actuated while the other one or two may remain neutral. Additionally or alternatively, the subunits may have a different orientation of magnetization. For example, one unit may provide a magnetic field pointing upwards, whereas another unit may provide a magnetic field pointing downwards.

Thus, a well defined and predetermined magnetic field and/or magnetic field gradient may be provided at the sensor surface in order to drive the magnetic label particles to specific binding sites or away therefrom.

If the subunits comprise electromagnets, it is further possible to generate a dynamic magnetic field, e.g. a rotating magnetic field.

According to a preferred embodiment, the quadrupole magnetic unit comprises four electromagnetic coils with a core, wherein the cores of the four electromagnetic coils have a shape adapted to provide a high magnetic field gradient at the sensor surface. This may be achieved, e.g., by providing a core with a sharp tip close to the sensor surface. It is also preferred that the cores of the four electromagnetic coils have a shape adapted to provide a high magnetic field gradient in a direction perpendicular to the sensor surface. It is particularly preferred that the cores of the four electromagnetic coils have a shape adapted to provide a low magnetic field gradient in a direction parallel to the sensor surface. This is preferably achieved by the cores of the four electromagnetic coils each having a sloped pole tip. According to a preferred embodiment, the slope of the pole tips has an angle of between 30° and 60°, preferably between 40° and 50° and most preferably of about 45° with respect to the sensor surface.

According to another preferred embodiment of the present invention, the quadrupole magnetic unit is moveable with respect to the sensor surface. It is in particular preferred that the quadrupole magnetic unit is slidable parallel to the sensor surface. Thus, a proper alignment between the binding sites of the sensor surface and the subunits of the quadrupole magnetic unit is possible.

It is also preferred that the quadrupole magnetic unit is adapted to provide a switchable magnetic field gradient.

The sensor surface of the biosensor preferably comprises one or more binding sites, wherein the one or more binding sites contain a reagent or a combination of several reagents.

The biosensor according to the present invention is advantageous over the prior art since it allows for a more accurate and precise actuation of magnetic label particles towards a sensor surface. Thus, more complex actuation schemes may be achieved including multi-step actuations towards different sensor sites on one and the same sensor surface. Furthermore, dynamic effects may be achieved by providing a rotating magnetic field or a high-switchable gradient. This helps inter alia to prevent the formation of vertical or horizontal pillars of superparamagnetic beads.

These and other aspects of the invention will be apparent from and elucidated with reference to the embodiment(s) described hereinafter.

DETAILED DESCRIPTION OF EMBODIMENTS

Figure 1:
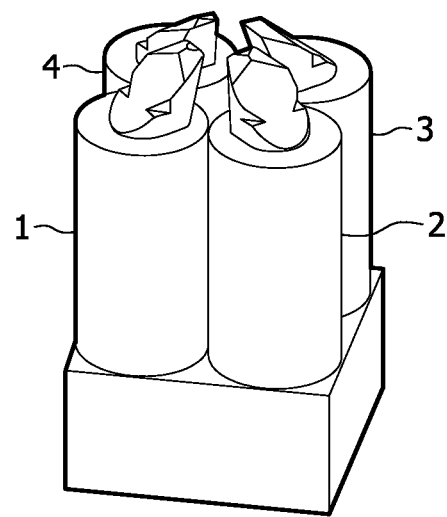
FIG. 1 shows a perspective view of a quadrupole magnetic unit which may be used in a biosensor according to the present invention.

FIG. 1 shows a perspective view of a quadrupole magnetic unit comprising four magnetic subunits 1, 2, 3 and 4, each consisting of an electromagnetic coil with a core. The cores are shaped to provide a high magnetic field gradient at a sensor surface to be located above the quadrupole magnetic unit. The cores of the four electromagnetic coils are separated by gaps. It is thus possible to perform detection, e.g. via FTIR, from the bottom of the sensor surface. An illumination light beam may be passed from below through a gap between two cores of the electromagnetic coils towards the sensor surface and light reflected by the sensor surface may be detected at a detector.

Figure 2:
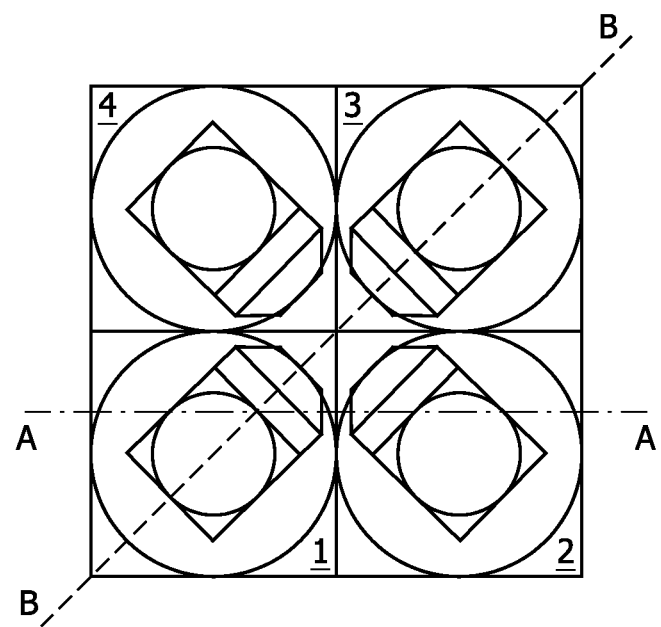
FIG. 2 is a top view of the quadrupole magnetic unit shown in FIG. 1.

FIG. 2 shows a top view of the quadrupole magnetic unit shown in FIG. 1. The gaps between the four cores are clearly visible.

Figure 3A:
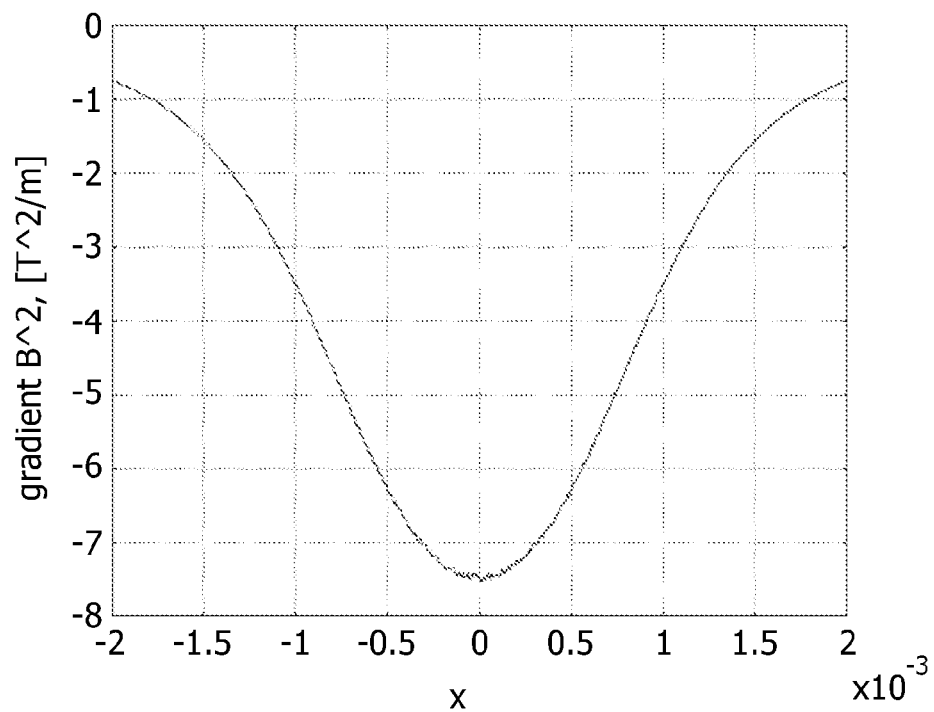
FIGS. 3a and 3b show exemplary gradients of $B^2$ which may be achieved by the quadrupole magnetic unit shown in FIGS. 1 and 2.

FIG. 3 shows the result of calculations of the gradient of $B^2$ which is induced by the quadrupole magnetic unit shown in FIGS. 1 and 2. The calculations are performed at a distance of 1 mm above the magnetic poles. FIG. 3a shows the gradient of $B^2$ in units of $T^2/m$ along line A-A in FIG. 2. Therein, magnetic subunit 1 provides a North pole, magnetic subunit 2 provides a South pole and magnetic subunits 3 and 4 are neutral.

Figure 3B:
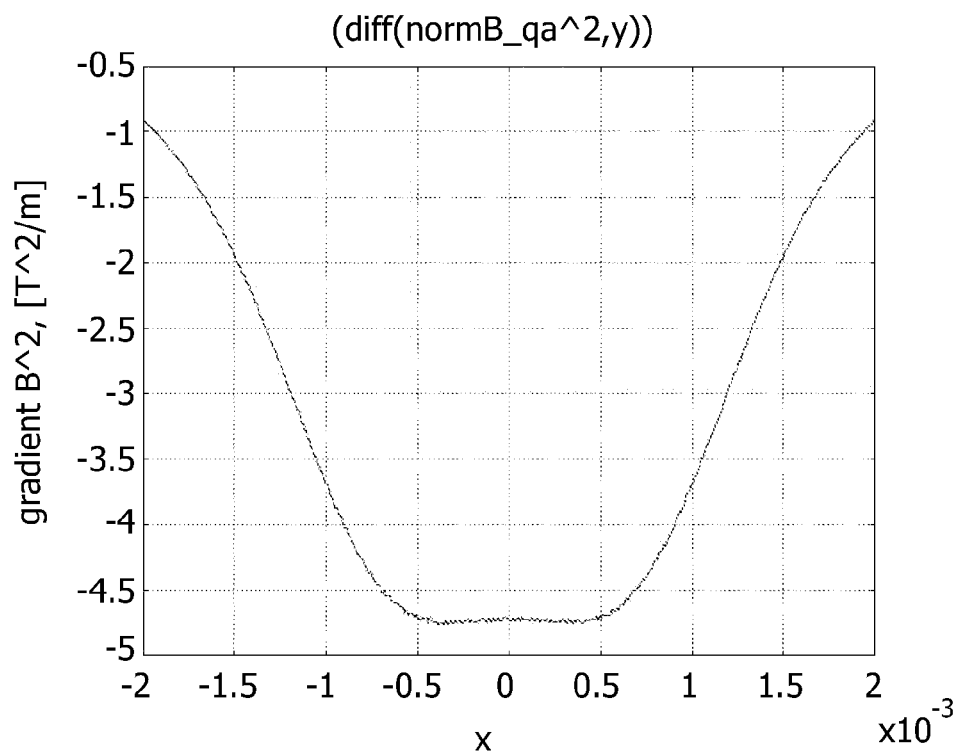

FIG. 3b shows the gradient of $B^2$ in units of $T^2/m$ along line B-B in FIG. 2. Here, magnetic subunit 1 is a North pole, magnetic subunit 3 is a South pole and magnetic subunits 2 and 4 are neutral. The maximum electric current applied is 1 A.

As can be seen from the two exemplary gradients shown in FIGS. 3a and 3b one can easily provide different magnetic field configurations by switching on and off different magnetic subunits. For example, the gradient of $B^2$ shown in FIG. 3a comprises a sharp minimum, whereas the gradient shown in FIG. 3b has an extremely broad minimum. Accordingly, the regions or binding sites, towards which magnetic particles are actuated, can be precisely construed.

Other effects are possible by providing, e.g., a rotating magnetic field. For this purpose, the four coils of the quadrupole magnetic unit are driven with, e.g., a sine wave current of maximum 1.5 A with 90° phase shift between each other.

It should be apparent to the skilled person that the above examples shall not be construed as limiting the scope of protection of the present invention. In fact, in a typical experiment using the biosensor of the present invention, a large amount of quite different actuations of the quadrupole magnetic unit may be performed. This may include different static and dynamic actuation schemes. Furthermore, the quadrupole magnetic unit is not limited to the unit shown in FIGS. 1 and 2. Any kind of a quadrupole arrangement of magnetic units may be used for the biosensor according to the present invention. In particular, the cores of the electromagnetic coils may have a varying shape depending on the particular application.

Figure 4:
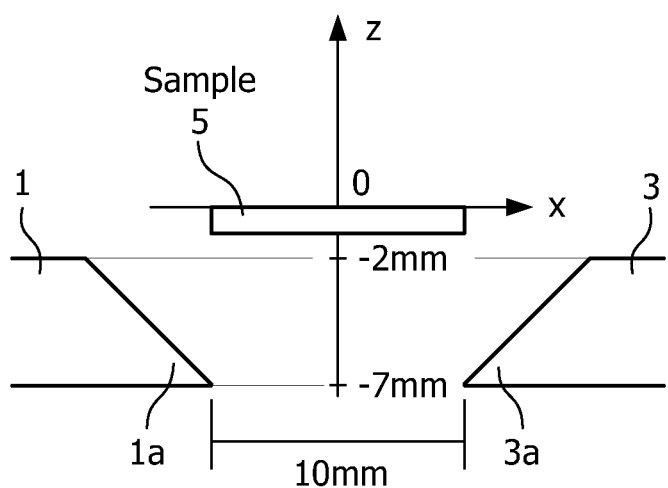
FIG. 4 shows a cross-sectional view of a quadrupole magnetic unit which may be used in a biosensor according to the present invention.

FIG. 4 shows a cross-sectional view of a preferred embodiment of a quadrupole magnetic unit which may be used in a biosensor according to the present invention. In the cross-sectional view, only two magnetic subunits 1 and 3 of the quadrupole magnetic unit can be seen. A complete top view of the magnetic quadrupole can be seen in FIG. 6. The magnetic quadrupole comprises four magnetic subunits 1, 2, 3 and 4, each of which comprise a bar made of soft iron with a coil around it and a pole tip (1a, 2a, 3a, 4a). Around those four magnetic subunits a flux guiding square 19 with a width of 115 mm is arranged. The flux guiding square 19 is also made of soft iron and has a cross-section of 10 mm×10 mm. The bars of the cores and the pole tips measure 5 mm×5 mm. Opposing pole tips are separated by 10 mm as can be seen in FIG. 4. In order to have a homogeneous field above the pole tips 1a and 3a, rather than inbetween, the pole tips 1a and 3a are sloped under an angle of 45°. Of course the corresponding pole tips 2a and 4a, which cannot be seen in FIG. 4, are sloped as well. The sample 5 is located at the center of the quadrupole, 2 mm above the top of the poles.

Figure 5:
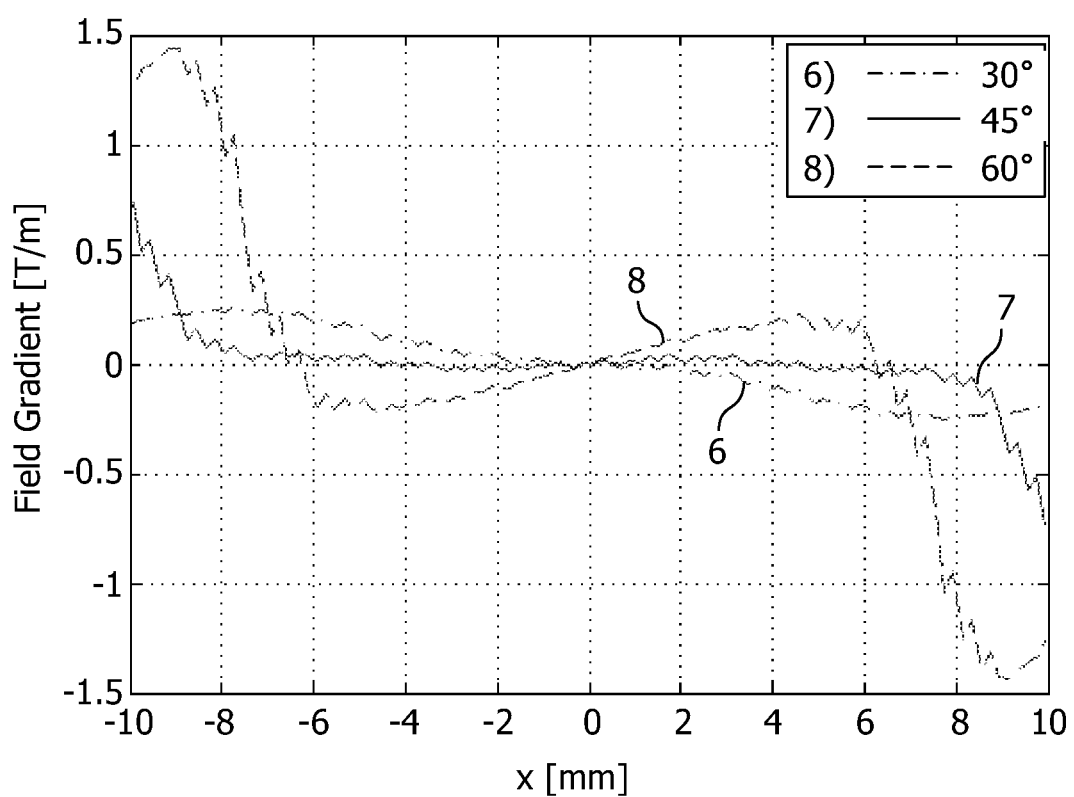
FIG. 5 shows simulations of the horizontal magnetic field gradient for different slopes of the pole tips of the quadrupole magnetic unit shown in FIG. 4.

Simulations show that pole tips sloped under 45° yield approximately the smallest horizontal field gradient. FIG. 5 shows a comparison of the simulated magnetic gradient for pole tips under an angle of 30° (curve 6), 45° (curve 7) and 60° (curve 8). The horizontal field gradient for pole tips having an angle of about 45° with respect to the sensor surface is clearly smaller than in the other two cases.

Figure 6:
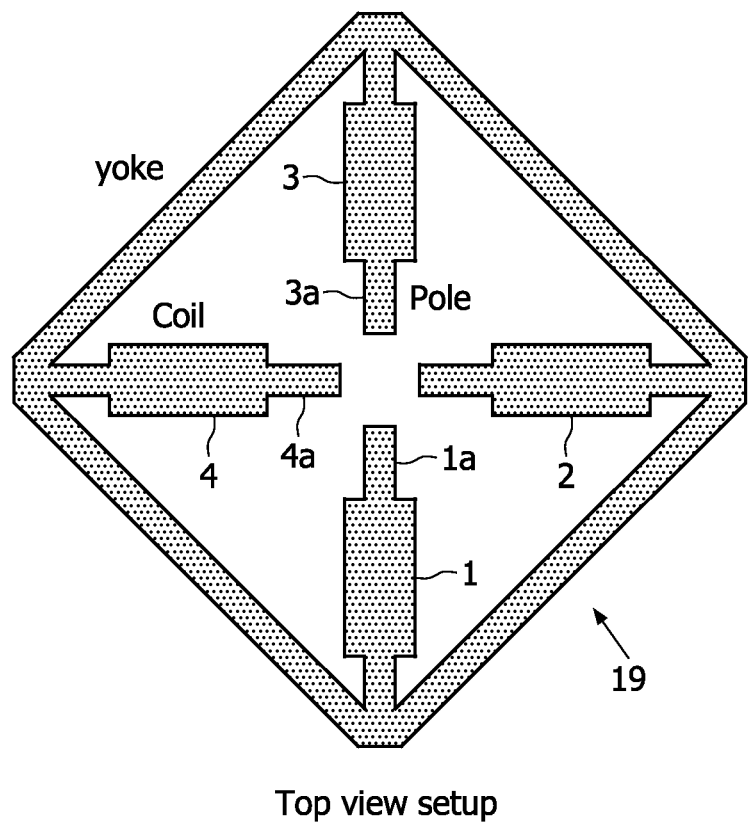
FIG. 6 shows a top view of the quadrupole magnetic unit shown in FIG. 4.
Figure 7A:
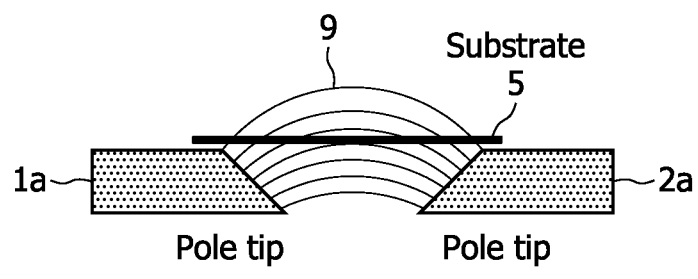
FIGS. 7a, 7b and 7c schematically show the flux lines of the magnetic field of the quadrupole magnetic unit shown in FIGS. 4 and 6 in cross-section and from a top perspective.
Figure 7B:
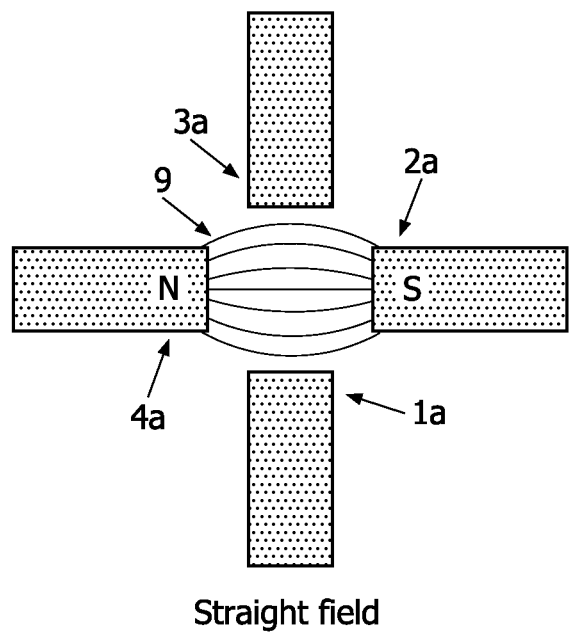
Figure 7C:
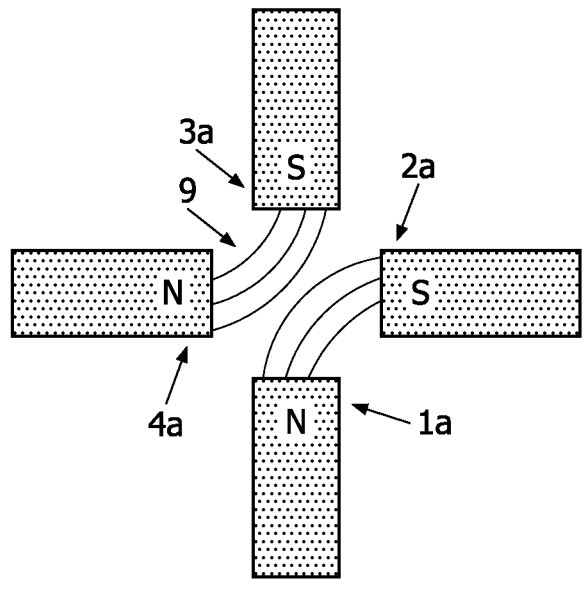

FIGS. 7a, 7b and 7c schematically show the flux lines 9 of the magnetic field of the quadrupole magnetic unit shown in FIGS. 4 and 6 in cross-section and from a top perspective. As can be taken from FIG. 7a, the magnetic field lines 9 are curved upwards because of the sloped pole tips. In FIG. 7a, a magnetic field between opposite poles 2a and 4a is simulated. In FIG. 7b, a magnetic field between adjacent poles 1a-2a and 3a-4a is simulated. It turns out that in the center of the quadrupole magnetic unit, namely in the optical field of view of the microscope, which measures approximately 0.1 mm×0.1 mm, the field lines 9 are substantially parallel to each other.

Figure 8A:
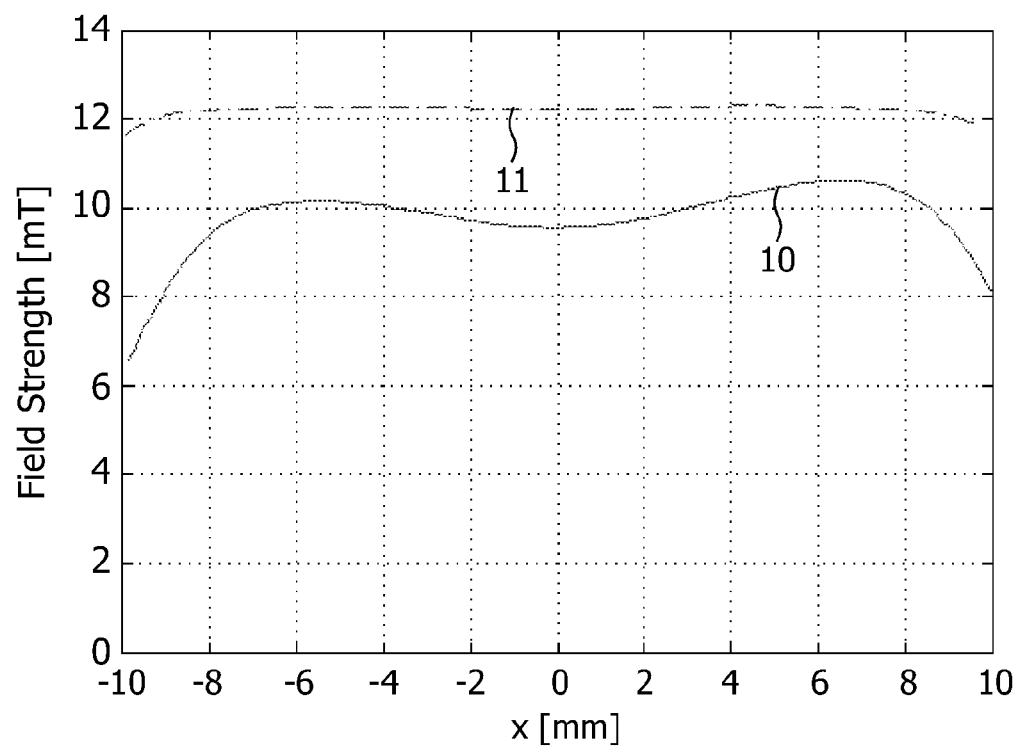
FIG. 8a shows a magnetic field strength as a function of the horizontal coordinate.

In order to determine the magnetic field gradients, the field strength was measured as a function of the horizontal coordinate x and the vertical coordinate z (compare FIG. 4). The magnetic field strength was measured with a Hall-sensor, while DC currents of +277 mA and −277 mA were applied through two opposite coils. The result of the measurement is shown in FIG. 8a as curve 10. Curve 11 represents a simulation.

Figure 8B:
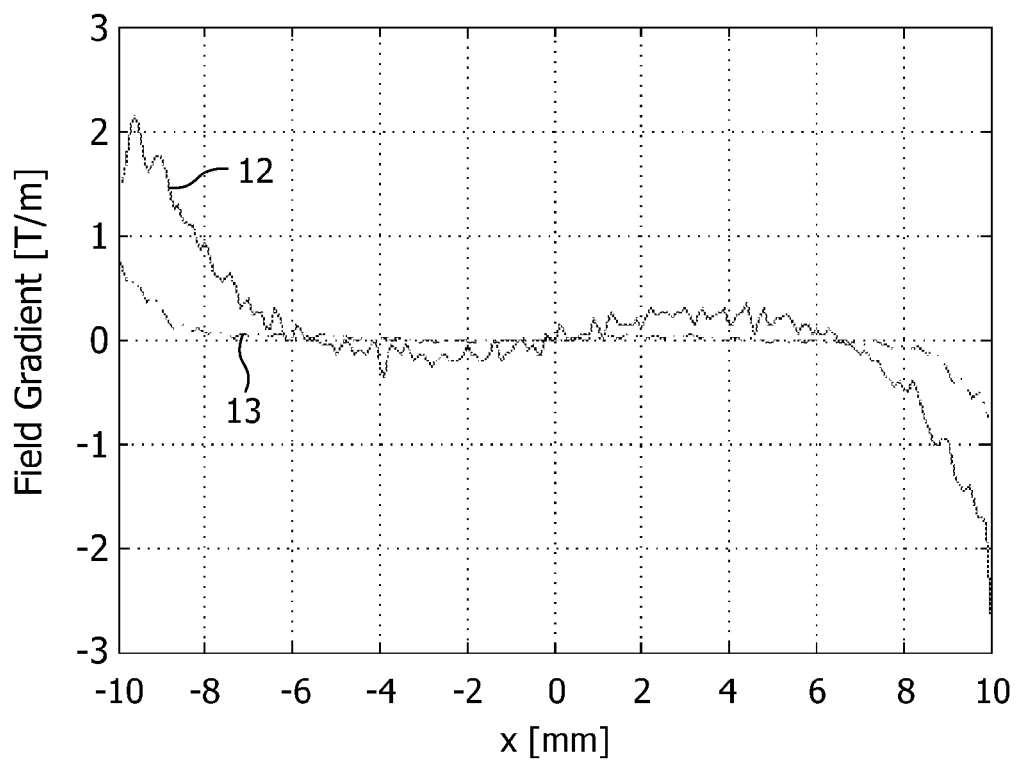
FIG. 8b shows the horizontal field gradient as a function of the horizontal coordinate.

In FIG. 8a, the field strength as a function of the horizontal coordinate x is shown. The small asymmetry in the field strength in the x-direction results from a slight asymmetry in the setup because the setup was not exactly level. The measured field strength is 20% lower than predicted by simulations because of the non-ideal properties of the real quadrupole compared to the simulations. FIG. 8b shows the horizontal magnetic field gradient as a function of the horizontal coordinate x both measured (curve 12) and simulated (curve 13).

Figure 9A:
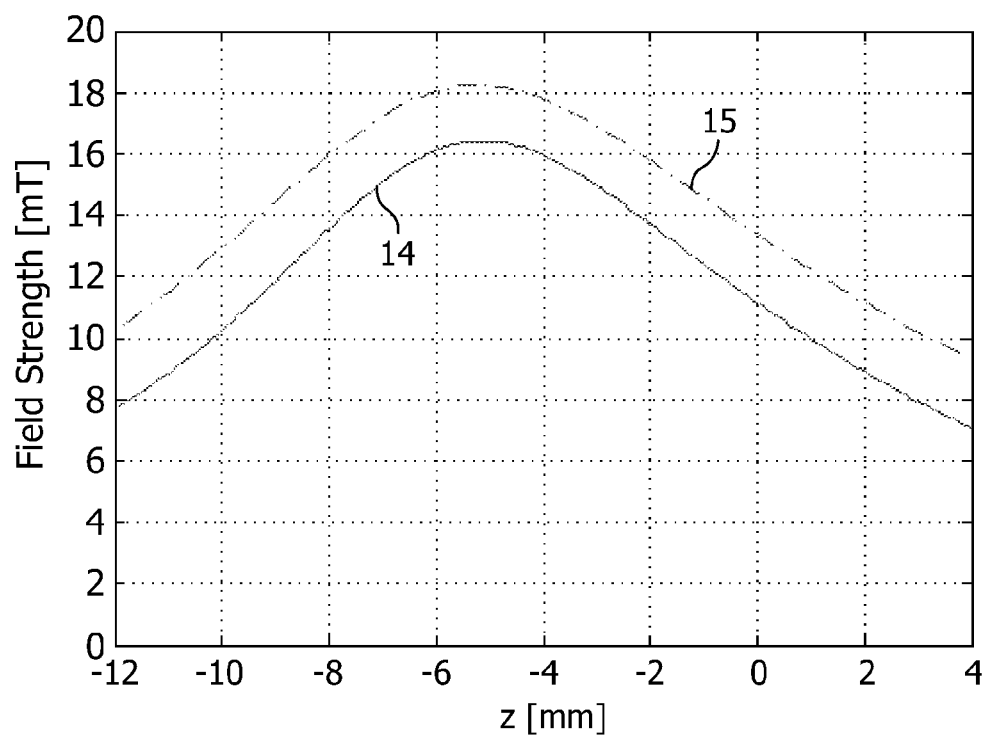
FIG. 9a shows the field strength as a function of the vertical coordinate.
Figure 9B:
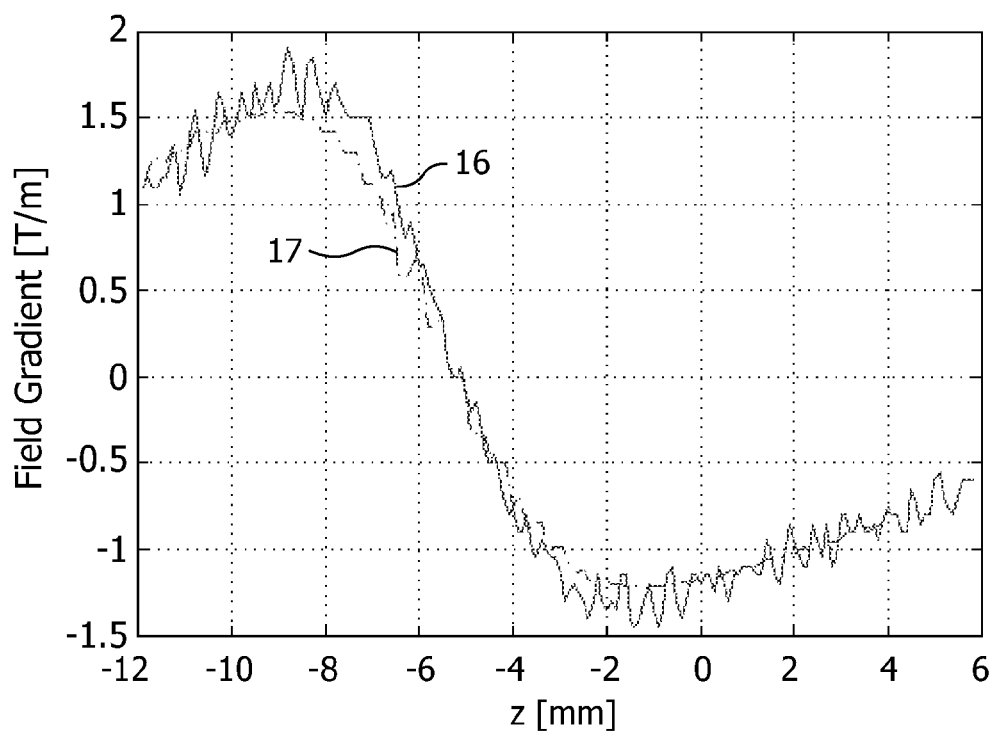
FIG. 9b shows the vertical field gradient as the function of the vertical coordinate.

FIG. 9a shows the magnetic field strength as a function of the vertical coordinate z (measurement: curve 14; simulation: curve 15), while FIG. 9b shows the vertical magnetic field gradient as a function of the vertical coordinate z (measurement: curve 16; simulation: curve 17).

As is apparent from the above results, using a quadrupole magnetic unit as shown in FIGS. 4 and 6 it is possible to provide at the same time a small magnetic field gradient parallel to the sensor surface and a large magnetic gradient perpendicular to the sensor surface. Accordingly, a large force in a direction perpendicular to the sensor surface can act on the magnetic beads of the magnetic biosensor. Thus, the magnetic beads can be effectively directed towards the sensors surface or away therefrom. At the same time, the lateral forces acting onto the beads are negligible. Therefore, the preferred embodiment shown in FIGS. 4 and 6 allows for a precise control of magnetic beads within the magnetic biosensor.

One of the advantages of the embodiment shown in FIGS. 4 and 6 is that homogeneous magnetic fields are generated in the optical field of view, with virtually absent horizontal gradient and a vertical gradient that yields forces on the beads on the order of magnitude of the gravitational force. Therefore, beads can be actuated and detected over a large area.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. Any reference signs in the claims should not be construed as limiting the scope.

The invention claimed is:

1. A biosensor comprising:
    a substrate for accommodating a fluid sample, the substrate having a sensor surface upon which one or more particles of the fluid sample are detectable,
    a quadrupole magnetic unit configured to provide a magnetic field gradient at the sensor surface, wherein the quadrupole magnetic unit is arranged below the sensor surface and comprises a hollow center and four magnetic subunits the four magnetic subunits each including a core with a pole tip disposed on the core, the pole tips being separated by gaps; and
    a light source disposed below the sensor surface and configured to pass a beam of light through one or more of the gaps between the pole tips to the sensor surface;
    a detector disposed above the sensor surface and configured to detect light reflected from the detector surface to detect particles either accumulated at or proximate to the sensor surface.

2. The biosensor according to claim 1, wherein the pole tips of the four electromagnetic coils are structured to provide substantially parallel magnetic field lines at the sensor surface.

3. The biosensor according to claim 2, wherein the pole tips of the four electromagnetic coils are structured to provide a magnetic field gradient with a strength of about 14 mT in a direction running perpendicular to the sensor surface.

4. The biosensor according to claim 3, wherein the pole tips of the four electromagnetic coils are structured to provide a magnetic field gradient with a strength of about 0 mT in a direction running parallel to the sensor surface.

5. The biosensor according to claim 1, wherein the pole tips are sloped at an angle of between 30° and 60° with respect to a horizontal plane running along the sensor surface.

6. The biosensor according to claim 1, further including a processor configured to provide a rotating magnetic field, wherein the processor drives an electric current to the magnetic subunits and the electric current includes a sine wave current with a 90 degree phase shift between each magnetic subunit.

7. The biosensor according to claim 1, further including a processor configured to provide a switchable magnetic field gradient, wherein the processor drives an electric current to each of the magnetic subunits individually.

8. The biosensor according to claim 1, wherein the sensor surface comprises at least one functionalized binding site for binding the one or more particles of the fluid.

9. The biosensor according to claim 8, wherein the at least one functionalized binding site contains at least one reagent.

10. A biosensor comprising:
    a substrate configured to receive a sample, the substrate including a sensor surface upon which one or more particles of the sample are detectable;
    a quadrupole magnet disposed below the sensor surface, wherein the quadrupole magnet comprises a hollow center and four magnetic subunits, each magnetic subunit including a pole tip, the pole tips being separated by gaps;
    a light source disposed below the sensor surface and configured to pass an illumination beam between one or more of the gaps between the magnetic subunits; and
    a particle detector disposed above the sensor surface and configured to detect the one or more particles of the fluid accumulating proximate to or at the sensor surface by detecting a reflected light emanating from the sensor surface.

11. The biosensor according to claim 10, further including a processor configured to provide a rotating magnetic field, wherein the processor drives an electric current to the magnetic subunits and the electric current includes a sine wave current with a 90 degree phase shift between each magnetic subunit.

12. The biosensor according to claim 10, wherein the quadrupole magnet is slidably mounted and configured to move along the horizontal plane running through the sensor surface.

13. The biosensor according to claim 10, further including a flux guiding square which surrounds the quadrupole magnet.

14. The biosensor according to claim 10, wherein the four magnetic subunits include two sets of opposing pole tips, the opposing pole tips separated by a distance of about 10 mm.

15. The biosensor according to claim 1, wherein the sensor surface is disposed approximately 2 mm above the pole tips of the magnetic subunits.

16. The biosensor according to claim 1, further including a means for controlling the magnetic units to generate a magnetic field between adjacent pole tips of the magnetic units including magnetic field lines which are substantially parallel at a horizontal position located in the center of the quadrupole magnetic unit.

17. The biosensor according to claim 1, further including means for applying currents to each of the magnetic subunits cores which cause the magnetic subunits to generate a first magnetic field gradient in a direction perpendicular to the sensor surface and a second magnetic field gradient parallel to the sensor surface and the pole tips are sloped with respect to the sensor surface, wherein the first magnetic field gradient is higher than the second magnetic field gradient.

* * * * *